United States Patent
Lee et al.

(10) Patent No.: US 10,709,757 B2
(45) Date of Patent: Jul. 14, 2020

(54) PHARMACEUTICAL COMPOSITION FOR ANTI-ANGIOGENESIS CONTAINING CYCLIC PENTADEPSIPEPTIDE AS AN EFFECTIVE INGREDIENT

(71) Applicant: CHUNG-ANG UNIVERSITY INDUSTRY-ACADEMIC COOPERATION FOUNDATION, Seoul (KR)

(72) Inventors: Chan Lee, Gyeonggi-do (KR); Sung-Kwon Moon, Chungcheongbuk-do (KR); Jee Taek Kim, Seoul (KR)

(73) Assignee: CHUNG-ANG UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 0 days.

(21) Appl. No.: 16/320,502

(22) PCT Filed: Feb. 6, 2018

(86) PCT No.: PCT/KR2018/001560
§ 371 (c)(1),
(2) Date: Jan. 25, 2019

(87) PCT Pub. No.: WO2018/147615
PCT Pub. Date: Aug. 16, 2018

(65) Prior Publication Data
US 2019/0351011 A1   Nov. 21, 2019

(30) Foreign Application Priority Data
Feb. 9, 2017  (KR) .......... 10-2017-0018103
Jan. 31, 2018 (KR) .......... 10-2018-0011886

(51) Int. Cl.
*A61K 38/15* (2006.01)
*A61P 27/02* (2006.01)

(52) U.S. Cl.
CPC .......... *A61K 38/15* (2013.01); *A61P 27/02* (2018.01)

(58) Field of Classification Search
CPC .................. A61K 38/15; A61P 27/02
See application file for complete search history.

(56) References Cited

U.S. PATENT DOCUMENTS

| | | | | |
|---|---|---|---|---|
| 9,145,442 B2* | 9/2015 | Lee | .......... | C07K 11/02 |
| 9,260,485 B2* | 2/2016 | Lee | .......... | C07K 11/02 |
| 2011/0269698 A1* | 11/2011 | Lee | .......... | C07K 11/02 |
| | | | | 514/19.9 |
| 2015/0025219 A1* | 1/2015 | Lee | .......... | C07K 11/02 |
| | | | | 530/317 |
| 2015/0191507 A1* | 7/2015 | Lee | .......... | C07K 11/02 |
| | | | | 435/71.2 |

FOREIGN PATENT DOCUMENTS

| | | |
|---|---|---|
| EP | 2 293 846 B1 | 7/2013 |
| KR | 10-2011-0076845 A | 7/2011 |
| KR | 10-1119561 B1 | 3/2012 |
| KR | 10-1120565 B1 | 3/2012 |

OTHER PUBLICATIONS

Effects of Epigallocatechin-3-gallate (EGCG) on A549 Lung Cancer Tumor Growth and Angiogenesis. Bioscience, Biotechnology, and Biochemistry, 2013. vol. 77, No. 9, pp. 1799-1803. (Year: 2013).*
Gavalas et al. Angiogenesis-Related Pathways in the Pathogenesis of Ovarian Cancer. Int. J. Mol. Sci. 2013, vol. 14, pp. 15885-15909. (Year: 2013).*
Song, et al., "A new cytotoxic cyclic pentadepsipeptide, neo-N-methylsansalvamide produced by Fusarium solani KCCM90040, isolated from potato," Food Chemistry, 2011, vol. 126(2), pp. 472-478.
Lee, et al., "Optimization of culture conditions of Fusarium solani for the production of neoN-methylsansalvamide," Biosci. Biotechnol. Biochem., 2014, vol. 78(8), pp. 1421-1427.

* cited by examiner

*Primary Examiner* — Marcela M Cordero Garcia
(74) *Attorney, Agent, or Firm* — Riverside Law LLP

(57) ABSTRACT

The present invention relates to a composition for inhibiting angiogenesis, containing neo-N-methylsansalvamide (NMSSV), which is a cyclic pentadepsipeptide, as an effective ingredient, and specifically, since the NMSSV of the present invention has excellent activity which inhibits cell migration and tube formation associated with angiogenesis, and concentration-dependently inhibits angiogenesis induced by a vascular endothelial growth factor, it is expected that the NMSSV of the present invention may inhibit angiogenesis and be usefully used as a therapeutic agent for various diseases in which angiogenesis is abnormally regulated.

7 Claims, 6 Drawing Sheets

Isolectin B4

PHARMACEUTICAL COMPOSITION FOR ANTI-ANGIOGENESIS CONTAINING CYCLIC PENTADEPSIPEPTIDE AS AN EFFECTIVE INGREDIENT

CROSS-REFERENCE TO RELATED APPLICATIONS

This application is the U.S. national phase application filed under 35 U.S.C. § 371 claiming benefit to International Patent Application No. PCT/KR2018/001560, filed on Feb. 6, 2018, which is entitled to priority under to Korean Patent Application No. 10-2017-0018103, filed Feb. 9, 2017 and Korean Patent Application No. 10-2018-0011886, filed Jan. 31, 2018.

CROSS-REFERENCE TO RELATED APPLICATION

This application claims priority to and the benefit of Korean Patent Application No. 10-2017-0018103 filed on Feb. 9, 2017 and Korean Patent Application No. 10-2018-0011886, filed on Jan. 31, 2018, the disclosure of which is incorporated herein by reference in its entirety.

TECHNICAL FIELD

The present invention relates to a pharmaceutical composition for anti-angiogenesis containing neo-N-methylsansalvamide (NMSSV), which is a cyclic pentadepsipeptide, as an effective ingredient.

BACKGROUND ART

Angiogenesis is a biological process of generating new blood vessels in a tissue or organ, and under normal physiological conditions, humans or animals generate new blood vessels only in very specific restricted situations. The angiogenesis occurs through a series of sequential steps including reconstructing vessels and generating new capillary vessels through decomposition of a vascular basement membrane by a proteolytic enzyme, proliferation and migration of the vascular endothelial cells that constitute vessel walls, and formation of a tube (a blood-vessel) by differentiating the vascular endothelial cells.

Further, the angiogenic process is strictly regulated by various negative and positive regulatory factors (Folkman and Cotran., Int. Rev. Exp. Patho., 16, 207~248, 1976), but if the angiogenesis is not normally regulated, it causes pathological disorders such as diabetic retinopathy, rheumatoid arthritis, inflammation, endometriosis, age-related vision deterioration, psoriasis, and hemangioma.

When major diseases associated with angiogenesis are classified, the diseases may be divided into inflammatory diseases such as arthritis, ophthalmological diseases such as diabetic retinopathy, dermatological diseases such as psoriasis, and cancer. Examples of an ophthalmological disease caused by angiogenesis include diseases such as macular degeneration, diabetic retinopathy, as a complication of diabetes, in which capillary vessels in the retina invade the vitreous body, and as a result, an eye becomes blind, retinopathy of prematurity, and neovascular glaucoma, and several millions of people globally lose their eyesight each year due to these diseases. In addition, an autoimmune disorder acts as a cause of arthritis, but it is known that chronic inflammation occurring in the synovial cavity induces angiogenesis as arthritis develops, and arthritis is a disease occurring when new capillary vessels invade the joints and the cartilage is destroyed. Furthermore, psoriasis is also a chronic proliferative disease occurring on skin, and since a lot of blood needs to be supplied for rapid proliferation of the disease, angiogenesis cannot help but to actively occur. Accordingly, the discovery of a material inhibiting neovascularization may also be widely used for the treatment of diseases such as diabetic retinopathy, rheumatoid arthritis, inflammation, endometriosis, age-related vision deterioration, psoriasis, and hemangioma, which are diseases associated with neovascularization, so that currently, the academic and industrial fields have been continuously conducting research and development on a novel material having these functions.

Furthermore, abnormal angiogenesis serves to supply nutrients and oxygen required for the growth and proliferation of a tumor, and new capillary vessels invading a tumor provide metastasizing cancer cells with an opportunity to enter the blood circulation system, thereby allowing the cancer cells to metastasize. Accordingly, studies on the mechanism of angiogenesis and development of a material capable of suppressing angiogenesis have been a focus of attention in the prevention and treatment of cancer, and recently, while the fact that the inhibition of tumor angiogenesis can effectively suppress the growth and development of a tumor and can prolong a patient's life in an animal cancer model and a human clinical experiment has been proven, studies on the development of an angiogenesis inhibitor have been actively conducted.

About 200 angiogenesis inhibitors developed until now have been reported, and the angiogenesis inhibitors can be largely classified into four angiogenesis inhibitor types which respectively play a role in the mechanism of decreasing the activity of a specific angiogenesis promoting factor, the mechanism of inducing the growth inhibition or apoptosis of vascular endothelial cells, the mechanism of inhibiting the action of indirect factors regulating an angiogenesis promoting factor or an endothelial cell survival factor, and the mechanism of increasing the activity of angiogenesis inhibitors present in vivo, and in particular, angiogenesis inhibitors such as angiostatin, endostatin, PK5, and prothrombin kringle 2 are well known (O'Relly, M. S. et al. Cell., 79, 315328, 1994; Lee. T. H., Biol. Che., 273, 28805~28812, 1998). However, even though various angiogenesis inhibitors in the related art are already known, the inhibitor has problems in that it is difficult to maintain an excellent activity for a long period of time, pharmaceutical characteristics are low, and the inhibitor may be easily denatured, so that there is a need for developing a new neovascularization inhibiting material.

Meanwhile, neo-N-methylsansalvamide (NMSSV), which is a cyclic pentadepsipeptide of the present invention, is a cyclic pentadepsipeptide in which the binding sequences of sansalvamide A (San A), N-methylsansalvamide, four constituent amino acids, and one hydroxy acid are different, and there is nothing known about the angiogenesis inhibition activity, which has not been reported from studies on sansalvamide A, N-methylsansalvamide, and homologues organically synthesized by using sansalvamide A and N-methylsansalvamide as a basic cyclic structure.

DISCLOSURE

Technical Problem

Thus, as a result of intensive efforts to find a material having the angiogenesis inhibition activity, the present inventors found, by confirming that cell migration and tube formation are concentration-dependently inhibited as a result of treating human umbilical vein endothelial cells (HUVECs) which are human vascular endothelial cells with neo-N-methylsansalvamide (NMSSV) and confirming that, in an animal model in which damage to the retina is caused by laser, the size of a lesion is decreased and the differentiation and migration of vascular endothelial cells are decreased according to the treatment with NMSSV, that the neo-N-methylsansalvamide (NMSSV) can be used as a composition for inhibiting angiogenesis and an effective ingredient of a therapeutic agent for disease, which can inhibit new blood vessels associated with macular degeneration, thereby completing the present invention.

Thus, an object of the present invention is to provide a pharmaceutical composition for inhibiting angiogenesis, including a cyclic pentadepsipeptide of the following Chemical Formula 1 as an effective ingredient.

[Chemical Formula 1]

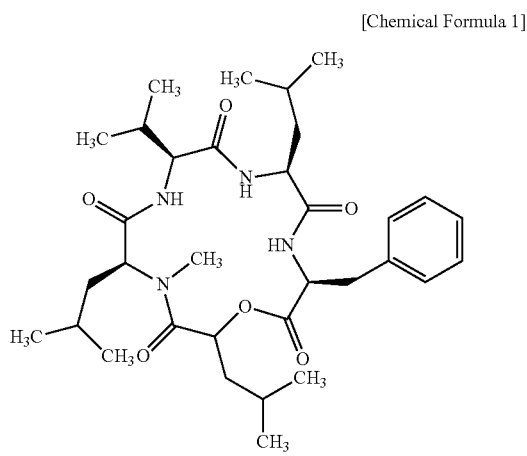 [SMILES: CC(C)CC1OC(=O)[C@H](Cc2ccccc2)NC(=O)[C@H](CC(C)C)NC(=O)[C@H](C(C)C)NC(=O)[C@H](CC(C)C)N(C)C1=O]

However, a technical problem to be achieved by the present invention is not limited to the aforementioned problem, and other problems that are not mentioned may be clearly understood by a person skilled in the art from the following description.

Technical Solution

In order to achieve the object, the present invention provides a pharmaceutical composition for inhibiting angiogenesis, including a cyclic pentadepsipeptide of the following Chemical Formula 1 as an effective ingredient.

[Chemical Formula 1]

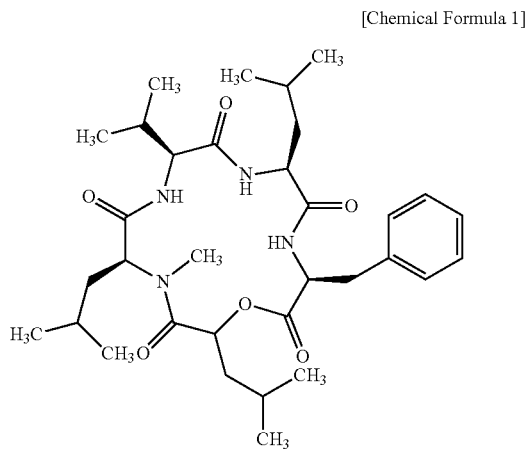 [SMILES: CC(C)CC1OC(=O)[C@H](Cc2ccccc2)NC(=O)[C@H](CC(C)C)NC(=O)[C@H](C(C)C)NC(=O)[C@H](CC(C)C)N(C)C1=O]

As an exemplary embodiment of the present invention, the composition may prevent or treat a disease caused by angiogenesis.

As another exemplary embodiment of the present invention, the disease may be arthritis, rheumatoid arthritis, chronic inflammation, osteoarthritis, diabetic retinopathy, retinopathy of prematurity, neovascular glaucoma, a corneal disease caused by neovascularization, macular degeneration, spot degeneration, pterygium, retinal degeneration, erythrosis, proliferative retinopathy, retrolental fibroplasia, granular conjunctivitis, capillarectasia, granuloma pyogenicum, psoriasis, seborrheic dermatitis, or acne.

As still another exemplary embodiment of the present invention, the cyclic pentadepsipeptide of Chemical Formula 1 may inhibit the proliferation of vascular endothelial cells.

As yet another exemplary embodiment of the present invention, the cyclic pentadepsipeptide of Chemical Formula 1 may inhibit the phosphorylation of extracellular signal-regulated kinase 1/2 (ERK1/2), protein kinase B (AKT) or endothelial nitric oxide synthase (eNOS) in vascular endothelial cells.

As yet another exemplary embodiment of the present invention, the cyclic pentadepsipeptide of Chemical Formula 1 may inhibit the cell migration of vascular endothelial cells.

As yet exemplary embodiment of the present invention, the cyclic pentadepsipeptide of Chemical Formula 1 may inhibit tube formation by differentiation of vascular endothelial cells.

Further, the present invention provides a health functional food for preventing and alleviating a disease associated with angiogenesis, which includes a cyclic pentadepsipeptide of the following Chemical Formula 1 as an effective ingredient.

[Chemical Formula 1]

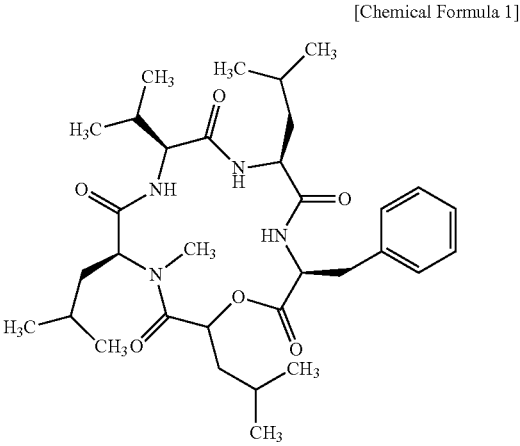 [SMILES: CC(C)CC1OC(=O)[C@H](Cc2ccccc2)NC(=O)[C@H](CC(C)C)NC(=O)[C@H](C(C)C)NC(=O)[C@H](CC(C)C)N(C)C1=O]

In addition, the present invention provides a method for treating an angiogenesis-related disease, the method comprising administering the pharmaceutical composition to a subject in need.

Furthermore, the present invention provides a use of the cyclic pentadepsipeptide of chemical formula 1 for producing a medicament for preventing or treating an angiogenesis-related disease.

Advantageous Effects

The present invention relates to a composition for inhibiting angiogenesis, containing neo-N-methylsansalvamide (NMSSV), which is a cyclic pentadepsipeptide, as an effective ingredient, and specifically, since the NMSSV of the present invention has excellent activity which inhibits cell migration and tube formation associated with angiogenesis, and concentration-dependently inhibits angiogenesis induced by a vascular endothelial growth factor, it is expected that the NMSSV of the present invention can inhibit angiogenesis and be usefully used as a therapeutic agent for various diseases in which angiogenesis is abnormally regulated, such as macular degeneration.

BEST MODE

Figure 1:
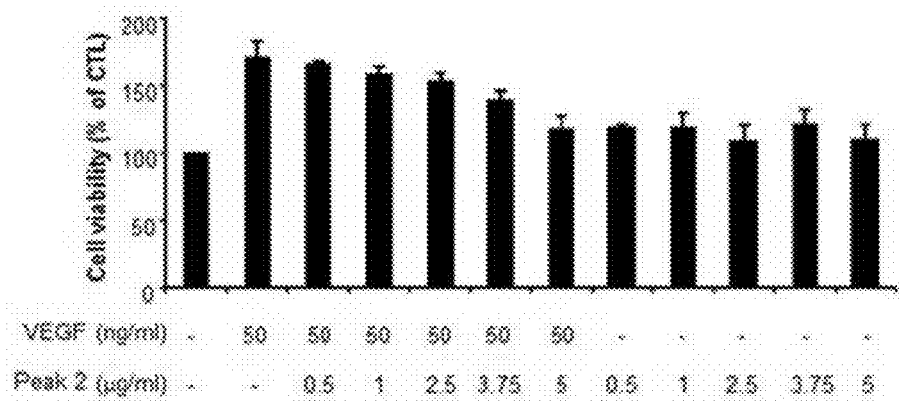
FIG. 1 is a graph confirming the effects of NMSSV on inhibition of VEGF-induced proliferation of HUVECs through MTT assay.

Based on the fact that neo-N-methylsansalvamide (NMSSV), which is a cyclic pentadepsipeptide, exhibits an activity inhibiting cell migration and tube formation associated with angiogenesis, the present inventors specifically identified concentration-dependent inhibition effects on vascular endothelial growth factor-induced angiogenesis by the NMSSV, and the like, thereby completing the present invention.

Hereinafter, the present invention will be described in detail.

The present invention provides a pharmaceutical composition for inhibiting angiogenesis, including a cyclic pentadepsipeptide of the following Chemical Formula 1 as an effective ingredient.

[Chemical Formula 1]

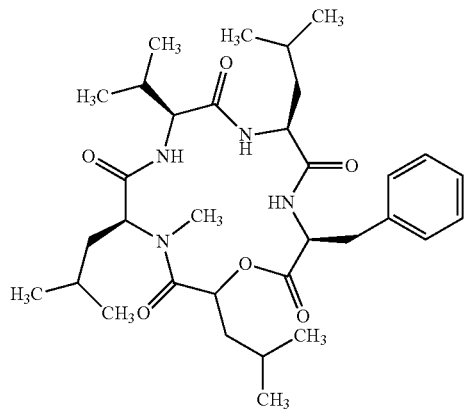

In the present invention, "a cyclic pentadepsipeptide" is a compound having the structure represented by Chemical Formula 1 and may be isolated from natural materials or artificially synthesized, and it is obvious to the person skilled in the art that even though being artificially synthesized, the cyclic pentadepsipeptide has the same effect.

In the present invention, "neo-N-methylsansalvamide (NMSSV)" is a cyclic peptadepsipeptide having 15 ring atoms, in which there is a difference in a binding sequence of sansalvamide A, N-methylsansalvamide, constituent amino acids, and hydroxy acid, which has been reported in the related art, and may be produced from *Fusarium solani* KCCM 90040 [Accession No.: KCCM10881P].

According to a preferred exemplary embodiment of the present invention, the pharmaceutical composition of the present invention may alleviate, prevent, or treat a disease caused by angiogenesis, and "an angiogenesis-related disease" or "a disease caused by angiogenesis", which is a disease to be alleviated, prevented, or treated by the composition of the present invention, refers to a disease caused by the abnormal progression of neovascularization. In the present specification, "the angiogenesis-related disease" and "the disease caused by angiogenesis" may be described interchangeably.

The angiogenesis-related disease capable of being prevented or treated by the composition of the present invention may be angiogenesis-dependent cancer, a benign tumor, arthritis, rheumatoid arthritis, chronic inflammation, osteoarthritis, diabetic retinopathy, retinopathy of prematurity, neovascular glaucoma, a corneal disease caused by neovascularization, macular degeneration, spot degeneration, pterygium, retinal degeneration, erythrosis, proliferative retinopathy, retrolental fibroplasia, granular conjunctivitis, capillarectasia, granuloma pyogenicum, psoriasis, seborrheic dermatitis, or acne, may be preferably an inflammatory disease, an ophthalmological disease, and/or a dermatological disease, which are/is caused by abnormal angiogenesis, and may be more preferably macular degeneration or arthritis, but is not limited thereto.

The cyclic pentadepsipeptide of the present invention may carry out treatment or prevention of an angiogenesis-related disease by inhibiting cell migration and tube formation by differentiation of vascular endothelial cells.

Meanwhile, the term "prevention" as used herein refers to all actions of inhibiting an angiogenesis-related disease or delaying the onset of the disease by administering the pharmaceutical composition according to the present invention.

Further, the term "treatment" as used herein refers to all actions in which symptoms of the angiogenesis-related disease are ameliorated or beneficially altered by administering the pharmaceutical composition according to the present invention.

In addition, the pharmaceutical composition according to the present invention may include a pharmaceutically acceptable carrier in addition to the effective ingredient. In this case, the pharmaceutically acceptable carrier is typically used during the formulation, and includes, but is not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil, and the like. Furthermore, the pharmaceutically acceptable carrier may further include a lubricant, a wetting agent, a sweetening agent, a flavoring agent, an emulsifier, a suspending agent, a preservative, and the like, in addition to the aforementioned ingredients.

The cyclic peptadepsipeptide represented by Chemical Formula 1 of the present invention may be used in the form of a pharmaceutically acceptable salt, and as the salt, an acid addition salt formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid or phosphorous acid, and nontoxic organic acids such as aliphatic mono- and dicarboxylates, phenyl-substituted alkanoates, hydroxyalkanoates and alkanedioates, aromatic acids, aliphatic and aromatic sulfonic acids. Such pharmaceutically nontoxic salts include sulfates, pyrosulfates, bisulfates, sulfites, bisulfites, nitrates, phosphates, monohydrogen phosphates, dihydrogen phosphates, metaphosphates, pyrophosphates, chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butene-1,4-dioates, hexane-1,6-dioates, benzoates, chlorobenzoates, methyl benzoates, dinitrobenzoates, hydroxybenzoates, methoxybenzoates, phthalates, terephthalates, benzenesulfonates, toluenesulfonates, chlorobenzenesulfonates, xylenesulfonates, phenyl acetates, phenyl propionates, phenyl butyrates, citrates, lactates, hydroxybutyrate, glycolates, malates, tartrates, methanesulfonates, propanesulfonates, naphthalene-1-sulfonates, naphthalene-2-sulfonates or mandelates.

The acid addition salt according to the present invention may be prepared by typical methods, for example, dissolving the cyclic pentadepsipeptide represented by Chemical Formula 1 in an excessive amount of aqueous acid solution, and precipitating this salt using a water-miscible organic solvent, for example, methanol, ethanol, acetone or acetonitrile. Further, the acid addition salt may also be prepared by evaporating the solvent or the excessive amount of acid from this mixture and drying the mixture or suction-filtering a precipitated salt.

In addition, a pharmaceutically acceptable metal salt may be prepared by using a base. An alkali metal or alkaline-earth metal salt is obtained by, for example, dissolving the compound in an excessive amount of alkali metal hydroxide or alkaline earth metal hydroxide solution, filtering the non-soluble compound salt, drying the filtrate, and drying the resulting product. In this case, preparing a sodium, potassium or calcium salt as the metal salt is pharmaceutically suitable. Furthermore, a silver salt corresponding to this is obtained by reacting the alkali metal or alkaline earth metal salt with a suitable silver salt (for example, silver nitrate).

The pharmaceutical composition of the present invention may be orally administered or may be parenterally administered (for example, applied intravenously, subcutaneously, intraperitoneally, or locally) according to a desired method, and the administration dose may vary depending on a patient's condition and body weight, severity of disease, drug form, and administration route and period, but it may be properly selected by the person skilled in the art.

The pharmaceutical composition of the present invention is administered in a pharmaceutically effective amount. In the present invention, "the pharmaceutically effective amount" refers to an amount sufficient to treat a disease at a reasonable benefit/risk ratio applicable to medical treatment, and the level of the effective dosage can be determined according to the type and severity of disease of a patient, the activity of the drug, the drug sensitivity in a patient, the administration time, the administration route and release rate, the treatment duration, factors including drugs that are simultaneously used with the composition of the present invention, or other factors well-known in the medical field. The pharmaceutical composition according to the present invention may be administered as an individual therapeutic agent or in combination with other therapeutic agents, may be administered sequentially or simultaneously with conventional therapeutic agents, and may be administered in a single dose or multiple doses. It is important to administer the composition in a minimum amount that can obtain the maximum effect without any side effects, in consideration of all the aforementioned factors, and this amount can be easily determined by the person skilled in the art.

Specifically, an effective amount of the pharmaceutical composition of the present invention may vary depending on the age, sex, condition, and body weight of a patient, the absorption rate of the active ingredients in the body, inert rate and excretion rate, disease type, and the drugs used in combination, and in general, 100 to 500 mg of the pharmaceutical composition of the present invention per 1 kg of a body weight may be administered daily or every other day or may be dividedly administered once to three times a day. However, since the effective amount may be increased or decreased depending on the administration route, the severity of obesity, the sex, the body weight, the age, and the like, the administration dose does not limit the range of the present invention in any manner.

Figure 6:
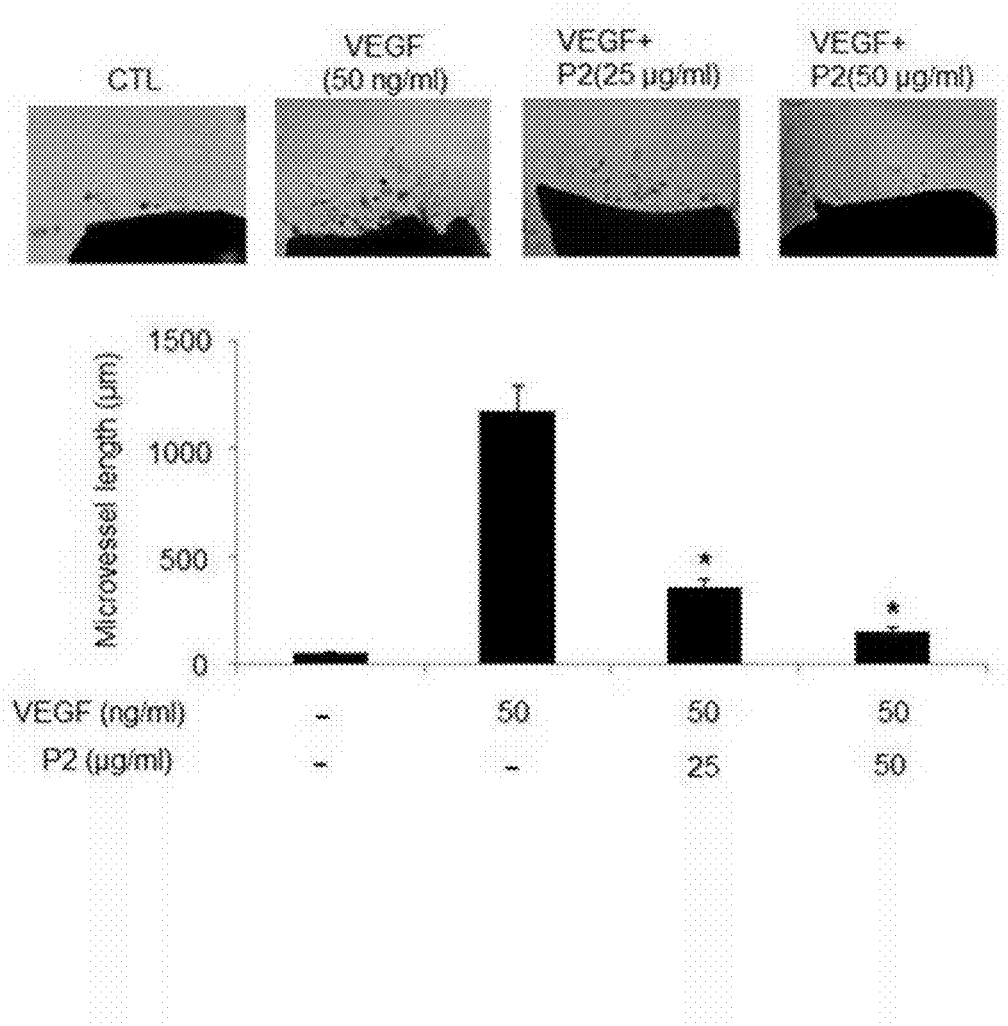
FIG. 6 includes images and a graph confirming the effects of NMSSV on inhibition of VEGF-induced angiogenesis ex vivo through an aortic ring assay.
Figure 7:
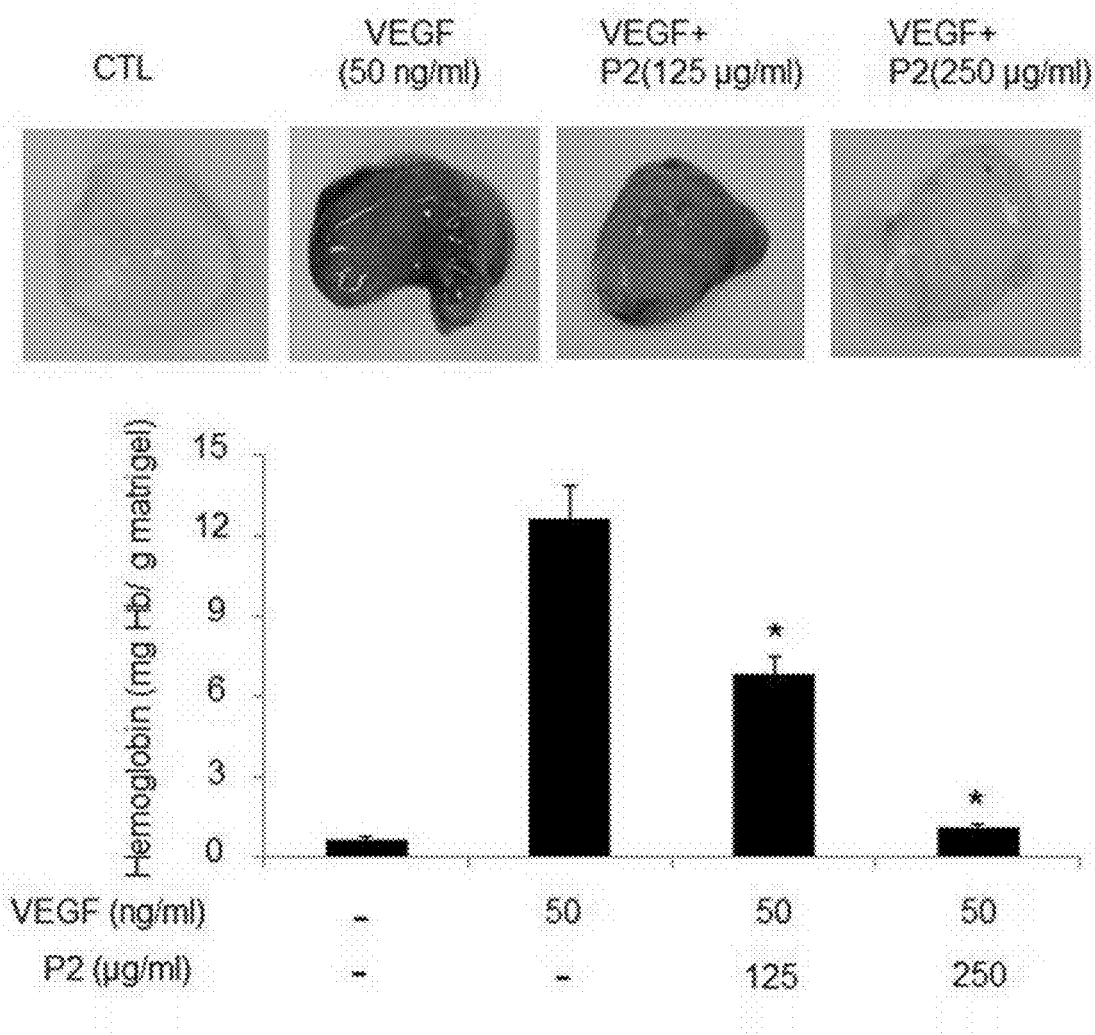
FIG. 7 includes images and a graph confirming the effects of NMSSV on inhibition of VEGF-induced angiogenesis in vivo through a Matrigel plug assay.

In a specific exemplary embodiment of the present invention, as a result of treating human umbilical vein endothelial cells which are human vascular endothelial cells (HUVECs) with NMSSV in order to confirm the effects of the cyclic pentadepsipeptide of the present invention on inhibition of cell migration and tube formation, the present inventors confirmed that tube formation (see FIG. 3) and cell migration (see FIG. 4) were concentration-dependently inhibited, and that a significant inhibition activity is exhibited against angiogenesis induced by a vascular endothelial growth factor (VEGF) (see FIGS. 6 and 7).

Figure 8:
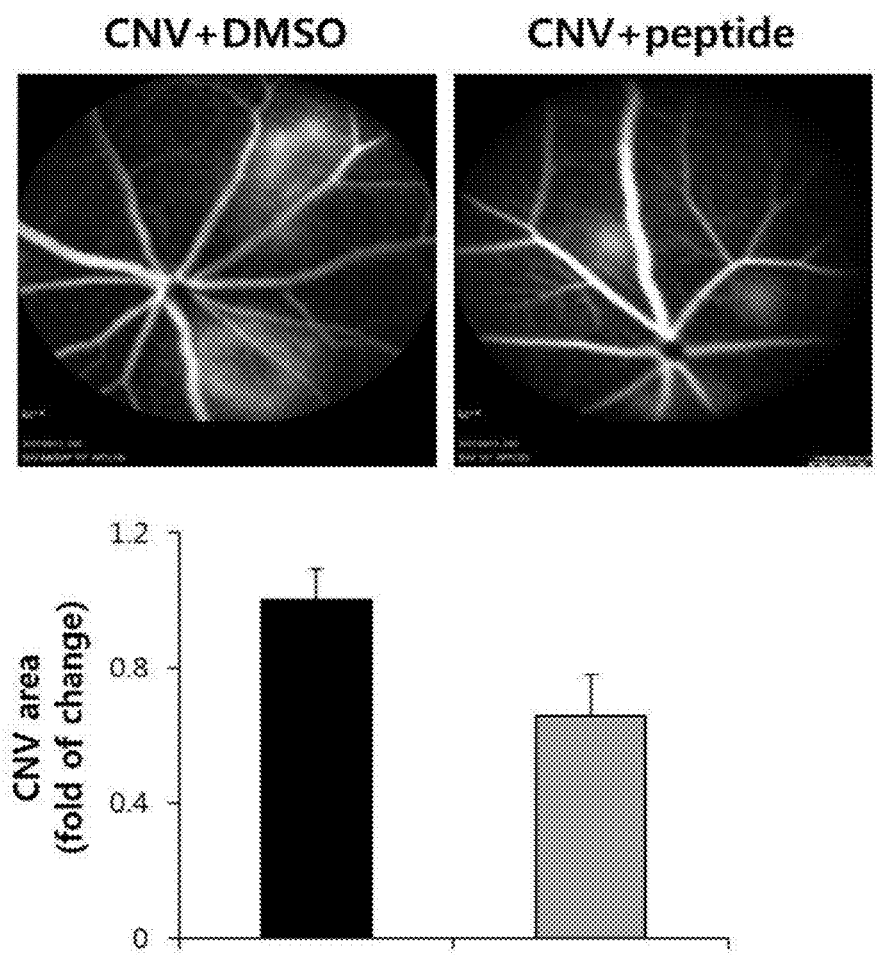
FIG. 8 includes images and a graph confirming a decrease in fluorescein leakage by administration of NMSSV in a CNV animal model through angiography.
Figure 9:
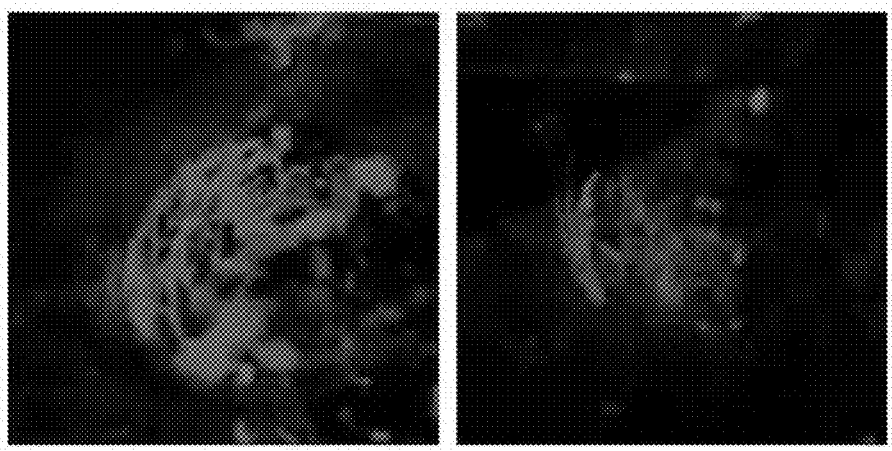
FIG. 9 includes images and a graph confirming a decrease in production of vascular endothelial cells by administration of NMSSV in a CNV animal model through immunofluorescence staining.
Figure 9:
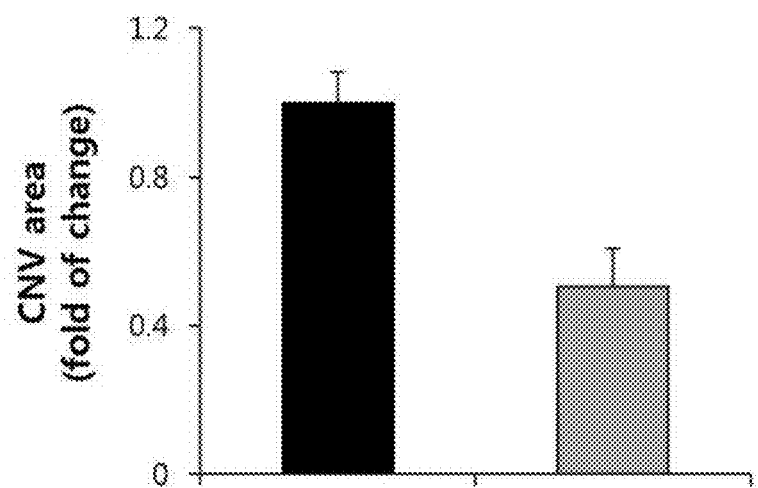

Further, through a specific exemplary embodiment of the present invention, as a result of manufacturing a CNV animal model in which choroidal neovascularization was induced by irradiation with laser and identifying the size of a lesion and the distribution of vascular endothelial cells according to the treatment with NMSSV, the present inventors found, by confirming that the size and/or degree of the lesion were/was decreased and vascular endothelial cells were distributed in a relatively narrow space according to the treatment with NMSSV, that NMSSV is therapeutically effective for a disease caused by angiogenesis and/or vascular injury in the retina and/or the choroid, such as macular degeneration by inhibiting an abnormal neovascularization and inhibiting the leakage of liquids from blood vessels (see FIGS. 8 and 9).

Accordingly, since the cyclic pentadepsipeptide of the present invention has excellent activity of inhibiting cell migration and tube formation, which are associated with angiogenesis and concentration-dependently inhibits angiogenesis induced by a vascular endothelial growth factor, the cyclic pentadepsipeptide of the present invention may be usefully used as an effective ingredient in a composition for inhibiting angiogenesis, and particularly, since the cyclic pentadepsipeptide of the present invention inhibits abnormal angiogenesis in the retina or the choroid and inhibits leakage from blood vessels, the cyclic pentadepsipeptide of the present invention may be usefully used in a composition for treating a disease caused by angiogenesis.

Thus, as another aspect of the present invention, the present invention may provide a health functional food composition for preventing or alleviating an angiogenesis-related disease, including a cyclic pentadepsipeptide of the following Chemical Formula 1 as an effective ingredient.

The term "alleviation" as used herein refers to all actions of at least reducing a parameter associated with a condition to be treated, for example, the degree of symptoms. In this case, in order to prevent or alleviate an angiogenesis-related disease, the health functional food composition may be used individually or simultaneously with a medicament for treatment prior to the onset step of the corresponding disease or after the onset of the corresponding disease.

The term "health functional food" as used herein refers to a food group to which an added value is imparted such that a function of the corresponding food can act or can be expressed for a particular purpose by using physical, biochemical, and biotechnological techniques, and the like, or a processed food designed to sufficiently express a body modulating function of the food related to biological defensive rhythm control, and prevention of and recovery from diseases, and the like in the body, and the health functional food may further include sitologically acceptable food supplementary additives and may further include appropriate carriers, excipients, and diluents typically used.

In addition, the health functional food composition of the present invention may contain various nutrients, vitamins, minerals (electrolytes), flavoring agents such as synthetic flavoring agents and natural flavoring agents, colorants, fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, and the ingredients may be used independently or in combination.

The composition may be included in an amount of 0.001 wt % to 90 wt %, preferably 0.1 wt % to 40 wt %, based on the total weight of the health functional food, and when the composition is used for long term ingestion, the amount may be equal to or less than the above range, but since the effective ingredient is not problematic in terms of safety, the composition may be used in an amount equal to or more than the above range, so that the amount is not limited to the above range.

As a still another aspect of the present invention, the present invention provides a method for treating an angiogenesis-related disease, the method including administering the pharmaceutical/food composition to an individual. In the present invention, "an individual" refers to a subject in need of treatment for a disease, and more specifically, refers to a mammal such as a human or a non-human primate, a mouse, a dog, a cat, a horse, and a cow.

Modes of the Invention

Hereinafter, preferred Examples for helping the understanding of the present invention will be suggested. However, the following Examples are provided only to more easily understand the present invention, and the contents of the present invention are not limited by the following Examples.

EXAMPLE

Example 1. Experimental Preparation and Experimental Method 1-1. Experimental Materials A human recombinant VEGF was purchased from R&D Systems (Minneapolis, Minn.), and ERK, phospho-ERK, AKT, phospho-AKT, eNOS, phospho-eNOS, and antibodies were purchased from Cell Signaling (Danvers, Mass.).

1-2. MTT Assay

After being cultured to 80-90% confluence, human umbilical vein endothelial cells (HUVECs) were additionally cultured in an M199 medium supplemented with 1% FBS for 6 hours, and then treated with neo-N-methylsansalvamide (NMSSV) at various concentrations in the presence of VEGF (50 ng/ml) for 24 hours. Effects of neo-N-methylsansalvamide (NMSSV) on the viability and growth inhibition of the HUVEC cells were measured by a 3-(4,5-dimethylthiazol-2-yl)-2,5-diphenyltetrazolium bromide (MTT) assay method.

1-3. Phosphorylation Assay of ERK1/2, AKT, and eNOS

After being cultured to 80-90% confluence, human umbilical vein endothelial cells (HUVECs) were additionally cultured in an M199 medium supplemented with 1% FBS for 6 hours, and then treated with neo-N-methylsansalvamide (NMSSV) at various concentrations in the presence of VEGF (50 ng/ml) for 10 minutes. Effects of neo-N-methylsansalvamide (NMSSV) in the phosphorylation assay of ERK1/2, AKT, and eNOS of HUVEC cells were measured by a Western assay method using each antibody.

1-4. Matrigel Plug Assay 1-4-1. Administration

A test material administration group and a VEGF (50 ng/ml) administration group were established, and each group consisted of six 8-week-old C57BL/6 mice. 0.5 ml of Matrigel, 50 U/ml of heparin, and a test material were formulated for use at each concentration right before the administration, and formulated such that VEGF was also included in the test material administration group. Seven days after the administration, a Matrigel plug was extracted, a photograph was taken, the amount of hemoglobin was measured by using the Drabkin method (Drabkin reagent kit 525, Sigma-Aldrich, Louis, Mo.), and purification was performed.

1-4-2. Administration Route 0.6 ml of the test material solution was administered to the dorsal hypodermis of each test animal by using a 1-ml syringe.

1-5. Wound-Healing Migration Assay

When cells were grown to approximately 90%, the medium was suctioned, and then a line was created by steadily scratching the bottom of the plate with a yellow tip, and then the cells were washed with PBS and treated with neo-N-methylsansalvamide (NMSSV) at various concentrations in the presence of VEGF (50 ng/ml) for 24 hours. After 24 hours, the tendency of cells to migrate at each treatment concentration was photographed and observed by marking the position under a microscope at 40× magnification.

1-6. Transwell Invasion Assay

An experiment was performed by using a modified Boyden chamber prepared with a polycarbonate nucleopore membrane (Corning, Corning, N.Y.). After trypsin-EDTA was added to the cells, the cells were collected, the cells were measured by using a hematocytometer, and then the concentration was set to $4 \times 10^5$ cells/ml, and the cells were respectively aliquoted. After 700 μl of the medium was added to the bottom well and an insert was placed thereon, 100 μl of cells prepared with neo-N-methylsansalvamide (NMSSV) at various concentrations were aliquoted into the insert in the presence of VEGF (50 ng/ml) and cultured in an incubator at 37° C. for 24 hours. After the incubation was completed, the cells of the insert which failed to pass through the gelatin of the upper chamber were wiped off with a cotton swab. After the cells, which succeeded in passing through the gelatin, were fixed with 4% paraformaldehyde, the cells were stained by using crystal violet, washed twice with PBS, and then placed on a glass plate. Thereafter, the cells were observed by using a microscope, and arbitrary five points were marked, photographed, and observed.

1-7. Aortic Ring Assay

150 μl of Matrigel was put into a 48-well plate, uniformly spread by shaking the 48-well plate, and hardened in an incubator at 37° C. for 30 minutes. After a C57BL/6 mouse was over-anesthetized with ether and sacrificed, the aorta was extracted and washed with PBS to remove the fat, the resulting aorta was transferred to human endothelial-SFM and excised by using micro scissors. The excised aorta was placed on the hardened Matrigel, 50 μl of Matrigel was dropped on the aorta tissue, and then hardened in an incubator at 37° C. for 30 minutes. 200 μl of a medium including neo-N-methylsansalvamide (NMSSV) and VEGF was each added, and cells were observed while being cultured in a $CO_2$ incubator at 37° C. After treatment with the test material, the cells were cultured for 14 days. On Day 7 and Day 14 of the culture, the cells were observed and photographed by an invert microscope (OLYMPUS, CKX41), and the lengths of the blood vessels produced were measured by photographing the aorta with the Toupview program (OLYMPUS, ver.3.5).

1-8. Colony Tube Formation Assay

After being cultured to 80-90% confluence in a plate covered with Matrigel (Collaborative Biomedical Products, Bedford, Mass.), HUVECs were additionally cultured in an M199 medium supplemented with 1% FBS for 6 hours, and then treated with neo-N-methylsansalvamide (NMSSV) at various concentrations in the presence of VEGF (50 ng/ml) for 24 hours. The tube formation was photographed by using a phase-contrast microscope.

1-9. Choroidal Neovascularization Inhibition Experiment 1-9-1. Preparation of Choroidal Neovascularization-Induced Animal Model A choroidal neovascularization (CNV)-induced mouse model was prepared by irradiation with laser, such that the model had a lesion similar to a Wet-AMD lesion. More specifically, male 6-week-old C57BL/6 mice were purchased from Orient Bio Inc., and acclimated for 1 week, and then anesthetized, and the pupils were dilated. Subsequently, an animal model was prepared by irradiating the space around the ophthalmic nerves in 12, 3, 6, and 9 o'clock directions with diode green laser (532 nm, 200 mW, 0.8 sec, 50 μm, and photocoagulator) to cause injury to 3 to 4 sites per eyeball.

1-9-2. Administration

After injury was caused to mice with laser by the method in Example 1-9-1 and the mice were anesthetized one day later, 2 μL was administered into the vitreous body of both eyes once (intravitreal injection) using a 34 gauge needle. Subsequently, 14 days after the irradiation with laser, angiography and staining and imaging of CNV were performed.

1-9-3. Angiography 14 days after the irradiation with laser, the mice experienced mydriasis and were systemically anesthetized by injecting 80 mg/kg of alfaxalone into the abdominal cavities of the mice, and then 1% fluorescein was intraperitoneally injected into the mice. And then, after the mice were photographed by using a Micron IV device, the CNV lesion area was measured by using Image-Pro Plus software.

1-9-4. Immunofluorescence Staining 14 days after the irradiation with laser, eyeballs were extracted from the mice, and then fixed in 4% paraformaldehyde for 1 hour. Thereafter, a retinal pigment epithelium (RPE)/choroid/sclera complex tissue was prepared by cutting and removing the corneas and the crystalline lenses with scissors, and carefully removing the retinas with pincers under a microscope. After the retinal flat mounted complex tissue was stirred in PBS supplemented with 5% bovine serum albumin and 0.5% Triton X-100 for 1 hour and washed, a reaction was performed at 4° C. overnight by diluting isolectin B4 (Invitrogen, USA) which is a vascular endothelial cell marker at a ratio of 1:100. Thereafter, after the complex tissue was washed with PBS, the tissue with a fluorescence mounting medium (Vector, USA) was fixed on a slide glass, and then covered with a cover slip, and the tissue was observed and photographed through a fluorescence microscope. The CNV lesion area was measured by using Image-Pro Plus software.

Example 2. Identification of Effects of Neo-N-Methylsansalvamide (NMSSV) on Inhibition of Vascular Endothelial Growth Factor (VEGF)-Induced Proliferation of Human Umbilical Vein Endothelial Cells (HUVECs)

In order to identify the effects of the neo-N-methylsansalvamide (NMSSV, Peak 2, hereinafter, referred to as P2) of the present invention on the proliferation in VEGF-induced HUVECs, it was confirmed that cells were proliferated by culturing the cells with P2 at various concentrations in the presence or absence of VEGF (50 ng/ml) by the method in Example 1-2 and performing an MTT assay 24 hours after the culture.

As a result, as illustrated in FIG. 1, it was confirmed that P2 dose-dependently inhibited the proliferation of HUVECs induced by VEGF, and furthermore, since significant apoptosis was not detected at 5 μg/ml of P2, the subsequent experiments were performed at less than 5 μg/ml, which is a non-cytotoxic concentration.

Example 3. Identification of Effects of NMSSV on Inhibition of Downstream Signaling in VEGF-Induced HUVECs First, a previous study proved the fact that in HUVECs, the extracellular signal-regulated kinase 1/2 (ERK1/2) and AKT/endothelial nitric oxide synthase (AKT/eNOS) pathways participate in an angiogenesis response to VEGF, so that the phosphorylation of ERK1/2, AKT, and eNOS was checked in order to identify the effects of P2 on downstream signaling molecules induced by VEGF in HUVECs. In this case, the HUVECs were pre-cultured for 10 minutes prior to the VEGF stimulation and along with P2 for 40 minutes.

Figure 2:
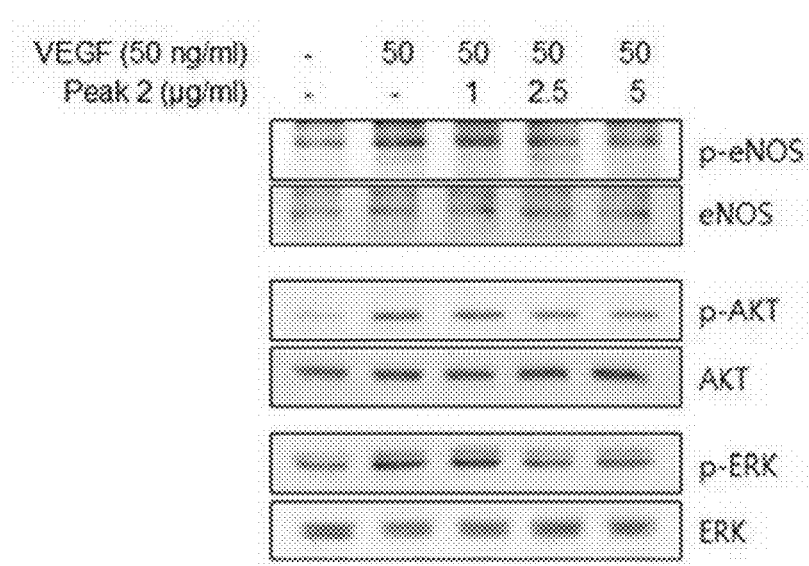
FIG. 2 is a diagram confirming the effects of NMSSV on inhibition of the phosphorylation of VEGF-induced ERK1/2, AKT, and eNOS of HUVECs.

As a result, as illustrated in FIG. 2, it was confirmed that P2 inhibited the phosphorylation of ERK1/2, AKT, and eNOS, which were induced by VEGF in HUVECs.

Example 4. Identification of Effects of NMSSV on Inhibition of Tube Formation, Migration, and Invasion in VEGF-Induced HUVECs The formation of capillary-like tubular structures by endothelial cells is one of the most essential steps in the development of angiogenesis, and it was checked whether P2 inhibited the formation of capillary-like network structures in HUVECs in Matrigel.

Figure 3:
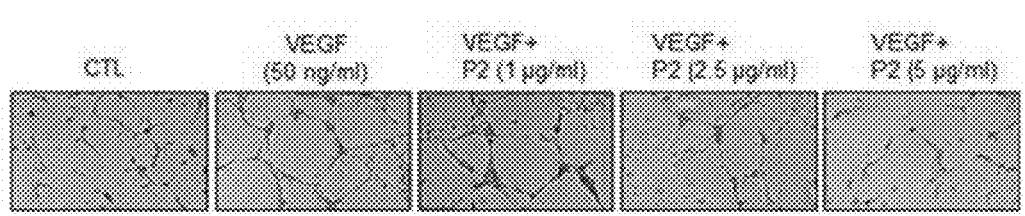
FIG. 3 includes images confirming the effects of NMSSV on inhibition of VEGF-induced colony tube formation of HUVECs.

As a result, as illustrated in FIG. 3, VEGF induced a vascular network in HUVECs in Matrigel, and the VEGF-induced colony tube formation in HUVECs was significantly inhibited by the addition of P2.

Subsequently, the migration and invasion of endothelial cells is also a main step of angiogenesis leading to the formation of new blood vessels, so that effects of P2 on mobility and invasiveness of VEGF-induced HUVECs were checked by using a wound-healing migration assay and a Transwell invasion assay.

Figure 4:
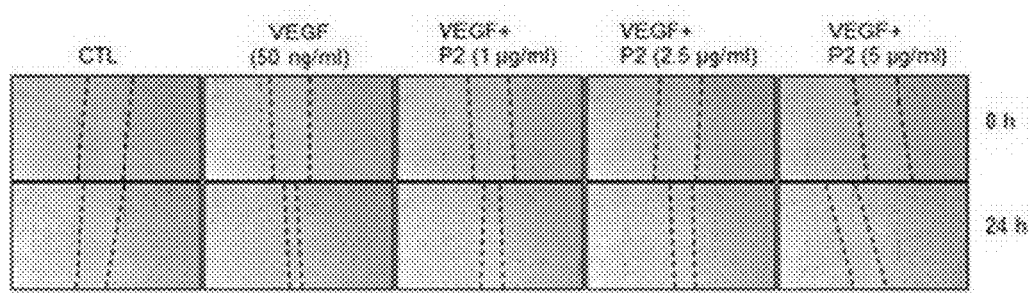
FIG. 4 includes images confirming the effects of NMSSV on inhibition of VEGF-induced cell migration of HUVECs.
Figure 5:
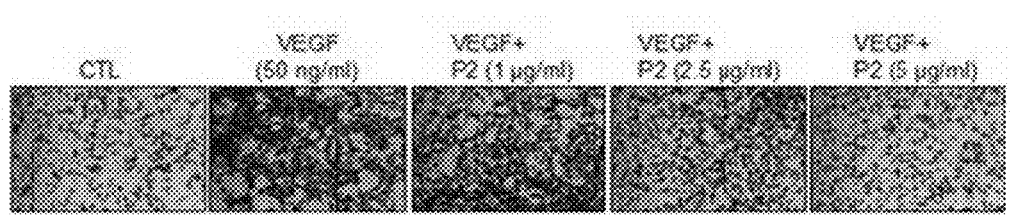
FIG. 5 includes images confirming the effects of NMSSV on inhibition of VEGF-induced invasion of HUVECs.

As a result, as illustrated in FIG. 4, during the treatment with P2, the VEGF-induced migration of HUVECs was significantly decreased, and also, as illustrated in FIG. 5, the invasion of HUVECs due to VEGF through Matrigel was blocked in the presence of P2.

The result suggests that P2 is effective for inhibiting colony tube formation, migration, and invasion of VEGF-induced HUVECs.

Example 5. Identification of Effects of NMSSV on Inhibition of Ex Vivo VEGF-Induced Vascularization and In Vivo Angiogenesis Based on the results in the Examples, the effects of P2 on ex vivo VEGF-induced neovascularization were identified, so that an aortic ring assay was performed in order to check the effects of P2 on the formation of capillary vessels in the presence of VEGF.

As a result, as illustrated in FIG. 6, it was confirmed that P2 significantly inhibited the formation of VEGF-induced blood vessels in a mouse aortic ring.

Thus, additionally through an in vivo Matrigel plug assay, the effects of P2 on in vivo angiogenesis were checked.

As a result, as illustrated in FIG. 7, it can be seen that the Matrigel containing VEGF exhibited a dark red color and was filled with blood vessels compared to the control, whereas the addition of P2 to the Matrigel turned the color into pale yellow, and the formation of new blood vessels was decreased compared to VEGF alone. Further, as a result of quantifying the formation of blood vessels of the Matrigel plug with the content of hemoglobin, it can be seen that P2 continuously inhibited the content of hemoglobin of a Matrigel plug treated with VEGF.

The result suggests that in both ex vivo and in vivo, P2 can inhibit the angiogenesis induced by VEGF.

Example 6. Identification of Effects of NMSSV on Inhibition of In Vivo Choroidal Neovascularization In CNV models in which angiogenesis was induced by irradiation with laser by the methods in Examples 1-9, the effects of administration of NMSSV on inhibition of angiogenesis were checked by imaging through angiography and staining.

More specifically, in mice in which choroidal neovascularization was induced by irradiation with laser, a contrast medium was leaked out from the retinal blood vessels due to destruction of the blood-retinal barrier, or the contrast medium was leaked from the choroid to the retina due to an abnormality of the retinal pigment epithelium layer, and the contrast medium leaked by the injury collects in a predetermined space such as a tissue or an intercellular space, or a dye is loosely attached to the tissue, so that fluorescence of the dye is abnormally decreased or exhibits a lost state (fluorescein leakage). Accordingly, in the animal models prepared by the methods in Examples 1-9, the degree to which the contrast medium was leaked according to the administration of NMSSV was compared with that of the control.

As a result, as illustrated in FIG. 8, the fluorescence of the dye in the group administered with NMSSV was more clearly observed than that of the control, meaning that the CNV lesion area is decreased by administration of NMSSV, and as a result, the fluorescein leakage was decreased.

In addition, in order to check the effects of administration of NMSSV as identified above on the decrease in the CNV lesion, an immunostaining experiment of isolectin B4 which is a vascular endothelial cell marker was performed. When 2 weeks had elapsed after CNV was induced by laser, crystalline lenses and vitreous bodies were removed by extracting eyeballs which were administered NMSSV and control eyeballs which were not administered NMSSV, and a retinal pigment epithelium-choroid-sclera tissue was obtained. The CNV areas of the control and the NMSSV-administered group were measured by measuring the areas dyed with isolectin B4 which is known as a marker specific to vascular endothelial cells. It was checked whether there was a change in CNV areas by measuring the areas of all the CNV lesions of each group to obtain an average value for each group.

As a result, as illustrated in FIG. 9, it was confirmed that the lesion area in the NMSSV-administered group after CNV was induced was significantly decreased compared to the lesion area of the control in which CNV was induced.

As can be seen from the above result, it can be confirmed that as a result of an experiment of inhibiting vascularization by using a CNV mouse model, NMSSV, which is a peptide isolated from potatoes, has a significant potential for use as a therapeutic agent for disease, which can inhibit neovascularization associated with macular degeneration.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

The present invention relates to a composition for inhibiting angiogenesis, containing neo-N-methylsansalvamide (NMSSV), which is a cyclic pentadepsipeptide, as an effective ingredient, and specifically, since the NMSSV of the present invention has excellent activity which inhibits cell migration and tube formation associated with angiogenesis, and concentration-dependently inhibits angiogenesis induced by a vascular endothelial growth factor, it can be widely used for treating angiogenesis-related diseases such as inflammatory diseases, ophthalmic diseases, skin diseases, and cancer, which cause abnormal angiogenesis or caused by thereof. Thus, the composition according to the present invention is expected to be used in various fields such as pharmaceuticals, outside medicinal agents, functional foods, and the like.

The invention claimed is:

1. A method for inhibiting angiogenesis, wherein the method comprises administering a pharmaceutical composition for inhibiting angiogenesis, comprising an isolated cyclic pentadepsipeptide of the following Chemical Formula 1 as an effective ingredient, to a subject in need thereof,

[Chemical Formula 1]

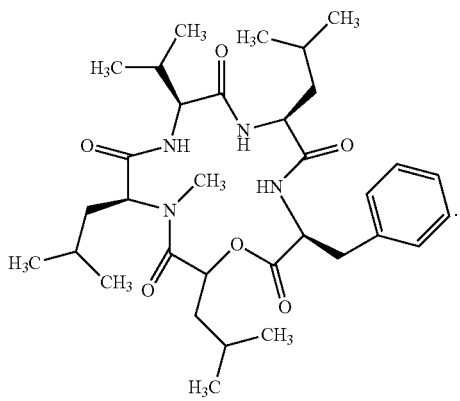

wherein the peptadepsipeptide inhibits the proliferation of vascular endothelial cells.

2. The method of claim 1, wherein the composition is capable of preventing or treating an angiogenesis-related disease.

3. The method of claim 2, wherein the disease is any one disease selected from a group consisting of arthritis, rheumatoid arthritis, chronic inflammation, osteoarthritis, diabetic retinopathy, retinopathy of prematurity, neovascular glaucoma, a corneal disease caused by neovascularization, macular degeneration, spot degeneration, pterygium, retinal degeneration, erythrosis, proliferative retinopathy, retrolental fibroplasia, granular conjunctivitis, capillarectasia, granuloma pyogenicum, psoriasis, seborrheic dermatitis, and acne.

4. The method of claim 1, wherein the isolated cyclic pentadepsipeptide of Chemical Formula 1 inhibits the phosphorylation of extracellular signal-regulated kinase 1/2 (ERK1/2), protein kinase B (AKT) or endothelial nitric oxide synthase (eNOS) in vascular endothelial cells.

5. The method of claim 1, wherein the isolated cyclic pentadepsipeptide of Chemical Formula 1 inhibits the cell migration of vascular endothelial cells.

6. The method of claim 1, wherein the isolated cyclic pentadepsipeptide of Chemical Formula 1 inhibits tube formation by differentiation of vascular endothelial cells.

7. A method for treating an angiogenesis-related disease, the method comprising administering a cyclic pentadepsipeptide of the following chemical formula 1 to a subject in need thereof,

[Chemical Formula 1]

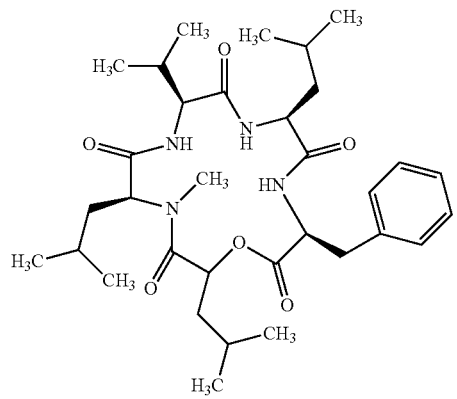

wherein the angiogenesis-related disease is any one disease selected from a group consisting of arthritis, rheumatoid arthritis, chronic inflammation, osteoarthritis, diabetic retinopathy, retinopathy of prematurity, neovascular glaucoma, a corneal disease caused by neovascularization, macular degeneration, spot degeneration, pterygium, retinal degeneration, erythrosis, proliferative retinopathy, retrolental fibroplasia, granular conjunctivitis, capillarectasia, granuloma pyogenicum, psoriasis, seborrheic dermatitis, and acne.

* * * * *